United States Patent [19]
Gustavson

[11] Patent Number: 5,108,432
[45] Date of Patent: Apr. 28, 1992

[54] POROUS FIXATION SURFACE

[75] Inventor: Larry J. Gustavson, Dover, N.J.

[73] Assignee: Pfizer Hospital Products Group, Inc., New York, N.Y.

[21] Appl. No.: 557,266

[22] Filed: Jun. 24, 1990

[51] Int. Cl.$^5$ .............................................. A61F 2/30
[52] U.S. Cl. ........................................ 623/16; 623/18; 623/20; 623/23
[58] Field of Search ................. 623/16, 18, 19, 20, 623/21, 22, 23

[56] References Cited

U.S. PATENT DOCUMENTS

| | | | |
|---|---|---|---|
| 3,605,123 | 9/1971 | Hahn | 623/16 |
| 3,855,638 | 12/1974 | Pilliar | 623/16 |
| 3,905,777 | 9/1975 | Lacroix | 29/183.5 |
| 3,938,198 | 2/1976 | Kahn et al. | 623/22 |
| 4,089,071 | 5/1978 | Kalnberz et al. | 623/18 |
| 4,261,063 | 4/1981 | Blanquaert | 623/18 |
| 4,536,894 | 8/1985 | Galante et al. | 623/22 |
| 4,542,539 | 9/1985 | Rowe et al. | 623/16 |
| 4,550,448 | 11/1985 | Kenna | 623/16 |
| 4,599,085 | 7/1986 | Riess et al. | 623/16 |
| 4,636,219 | 1/1987 | Pratt et al. | 623/18 |
| 4,644,942 | 2/1987 | Sump | 623/16 |
| 4,660,755 | 4/1987 | Farling et al. | 228/178 |
| 4,813,959 | 3/1989 | Cremascoli | 623/22 |
| 4,813,960 | 3/1989 | Muller | 623/22 |
| 4,854,496 | 8/1989 | Bugle | 228/193 |
| 4,863,474 | 9/1989 | Brown et al. | 623/16 |
| 4,863,475 | 9/1989 | Andersen et al. | 623/16 |

FOREIGN PATENT DOCUMENTS 0230006  7/1987  European Pat. Off. ............. 623/23

Primary Examiner—David Isabella
Attorney, Agent, or Firm—Peter C. Richardson; Lawrence C. Akers; Raymond W. Augustin

[57] ABSTRACT

A prosthetic part for use as an orthopedic implant has a base member defining an outer surface for implantation adjacent a prepared bone surface. The outer surface includes a recessed area having a predetermined shape and depth. A first rigid plate having this predetermined shape and having a plurality of elongated slots formed therein is fixedly attached within the recesssed area of the base member. A second rigid plate also having the same predetermined shape as the recess and also having a plurality of elongated slots formed therein is attached to the first rigid plate. The elongated slots of the second plate are angularly offset with respect to the elongated slots in the first plate to produce a controlled porosity. The thicknesses of the first and second plates are predetermined so that the outer surface of the second plate is continuous with the non-recessed outer surface of the base member.

20 Claims, 4 Drawing Sheets

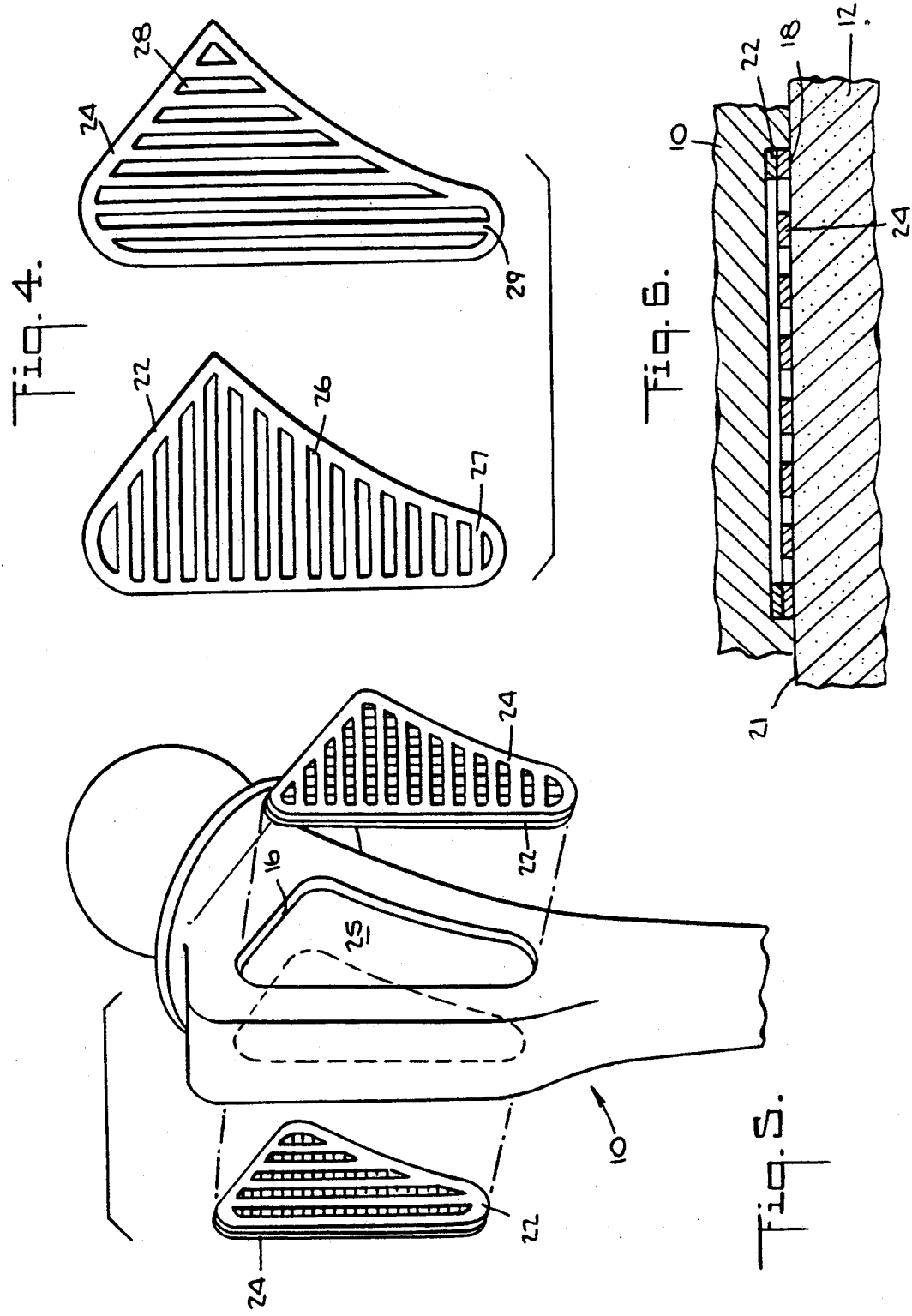

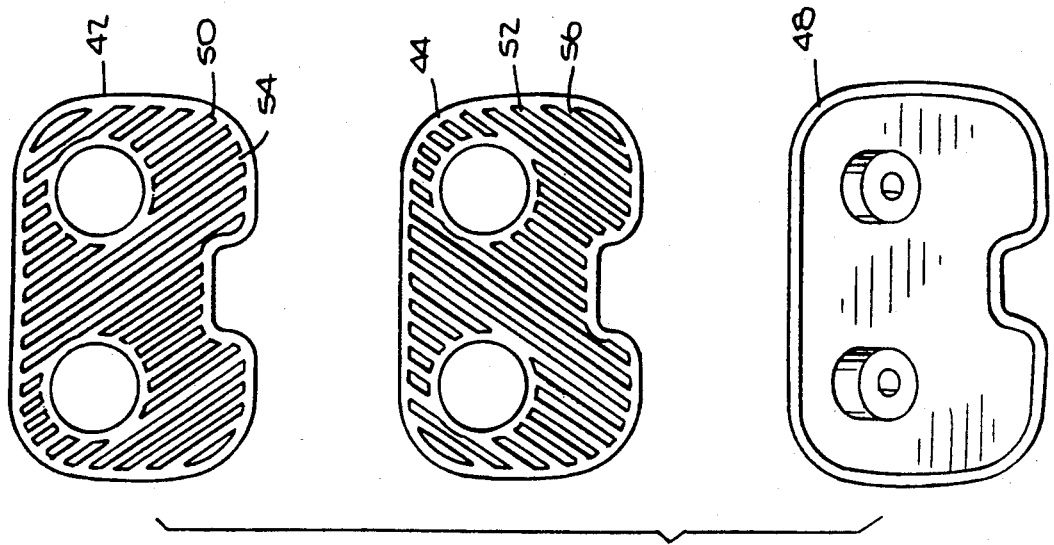
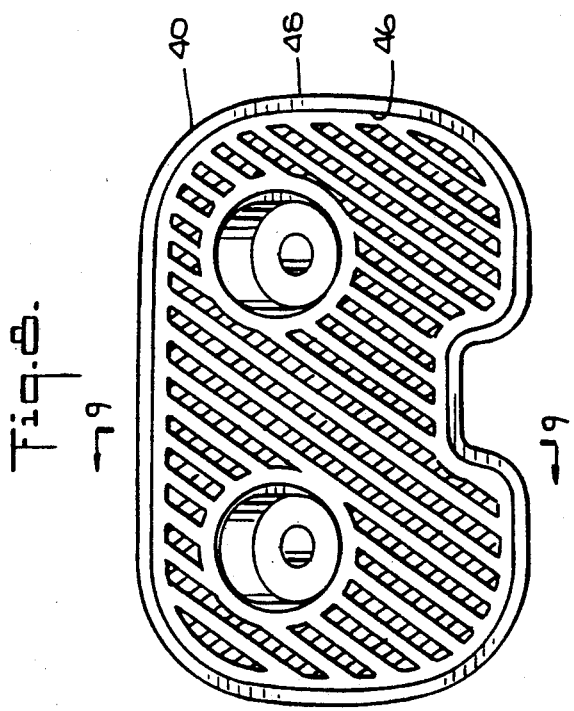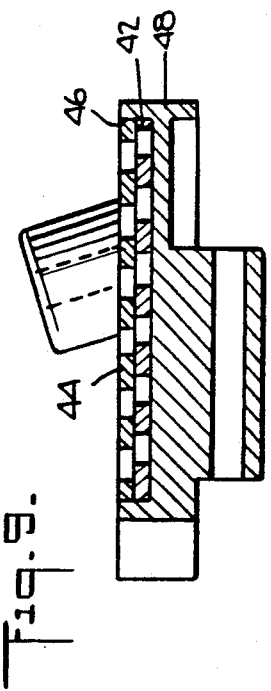

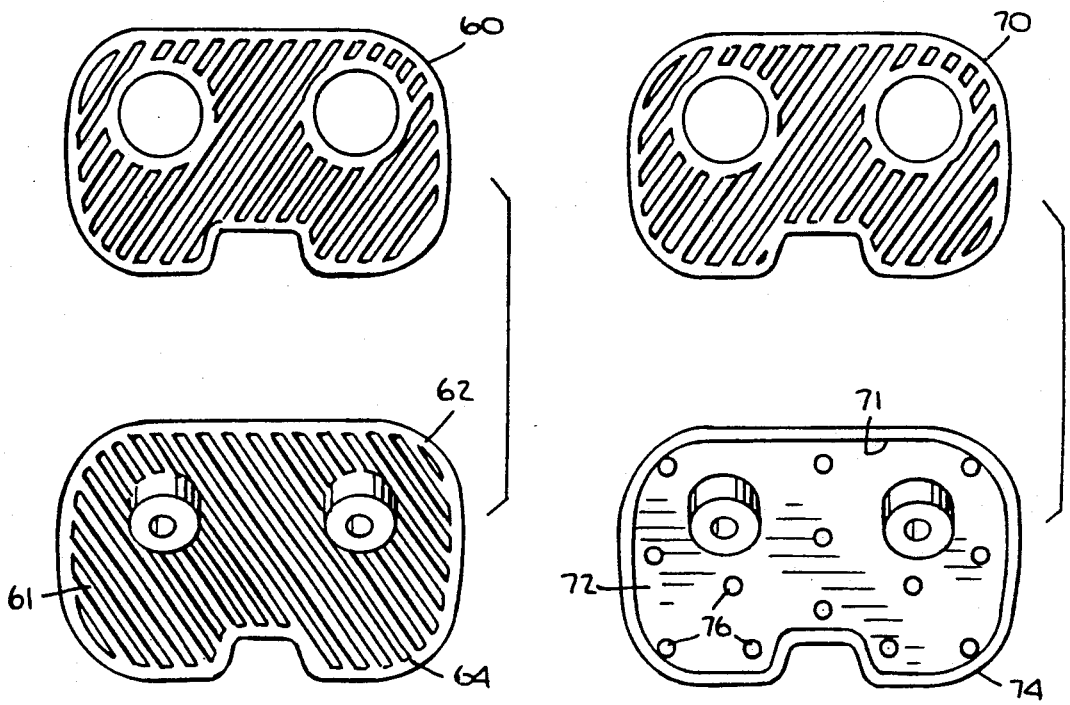

POROUS FIXATION SURFACE

BACKGROUND OF THE INVENTION

1. Field of the Invention

The invention relates to a skeletal prosthetic implant containing a bonded porous fixation structure on its surface. More particularly, the porous ingrowth structure is comprised of at least one slotted plate diffusion bonded to the surface of a metal prosthetic implant or bonded in a recess formed on the surface.

2. Description of the Prior Art

Tissue ingrowth surfaces intended to improve fixation of prosthetic implants have experienced increasing acceptance in the orthopedic field in recent years. In the past, most implants were fixed using a polymethyl methacrylate bone cement to achieve prosthesis fixation. However, recent experience has shown that fixation utilizing tissue ingrowth into porous coated implants has achieved success rates equivalent to prostheses fixed with cement.

In most cases, the porous structures or coatings utilized to create fixation by tissue ingrowth were loosely packed sintered metal powders, kinked pressed metal fibers, woven metallic meshes, or expanded metal sheets as well as porous polymeric materials.

Examples of tissue ingrowth surfaces in the form of meshes are shown in U.S. Pat. Nos. 3,905,777, 3,938,198, 4,089,071, 4,261,063, 4,536,894, 4,636,219, 4,644,942, 4,813,959, 4,813,960, 4,863,474 and 4,863,475.

Examples of metallic particles bonded to the surface of orthopedic implants to encourage tissue ingrowth are shown in U.S. Pat. Nos. 3,605,123, 4,542,539, 4,550,448 and 3,855,638. U.S. Pat. No. 4,599,085 relates to an implant member comprising sintered metal plus bioactive ceramics which encourage tissue ingrowth.

U.S. Pat. No. 4,660,755 relates to the use of resistance welding to bond meshes to a substrate.

U.S. Pat. No. 4,854,496, relates to a porous metal coated implant where spherical particles are diffusion bonded to an implant made from titanium.

Each of these structures has its own characteristic porosity, which is a function of the materials and processes used to create the structure. While porous structures may vary from coating to coating, within a given porous coating, the structural porosity is normally constant, and can be defined in terms of pore size, pore size distribution and overall pore volume. It is difficult to vary these structures to form a wide variety of pore sizes and pore size distributions.

Even in clinically successful uses of the prior art tissue ingrowth structures, the ingrowth of biological tissue is found to be somewhat sporadic in a variable composition and comprised of substantial amounts of soft connective tissues with only partial proportions of bone. Fixation is enhanced where larger amounts of bone or hard connecting tissue grows into the prosthesis surface rather than merely soft connective tissue. Laboratory histological examination of retrieved clinical human implants and experiments conducted in animals have shown that there is a relationship between the pore size and ingrown bone quality. It has been found that fine pores encourage soft connective tissue ingrowth while larger pores favor hard or bone tissue ingrowth. It has also been found that hard or dense cortical bone exhibits a faster ingrowth rate than spongy cancellous bone. In general, tissue ingrowth develops a preferential orientation in response to the direction of loading applied across the implant-bone interface.

The present invention utilizes these relationships between ingrowth tissue quality, coating pore size and the relationship of the loads applied between the prosthesis and bone interface to produce a porous ingrowth surface which can be easily tailored to take advantage of these known design parameters. The present invention, therefore, is in contrast with existing coatings. The prior art coatings offer no provision for tailoring the porous coating as necessary to address the variability of bone at the surgical sight or to achieve a preferred tissue orientation to resist anticipated in-service loading.

SUMMARY OF THE INVENTION

It is an object of this invention to provide a biocompatible, interconnected porous surface on prostheses for purposes of improved implant fixation, which surface is an integral part of the prosthesis.

A further object of the invention is to provide an attachment surface on the prosthesis which can be easily shaped to conform with the prosthesis surface and which allows for the easy variation of pore size.

It is yet a further object of the invention to provide a biocompatible porous surface in which the orientation of the pores may be controlled to promote tissue ingrowth in a manner to better resist forces applied from the bone interface to the prosthesis after implantation.

These and related objects are achieved in the present invention by a prosthetic part useable as an orthopedic implant which includes a base member having an outer surface for implantation adjacent a prepared bone surface. A spacer is integrally attached to at least a portion of the outer surface of the base member and at least one rigid plate having a plurality of openings therethrough is then fixedly attached to the spacer. The at least one rigid plate has an outer surface spaced a predetermined distance from the outer surface of the base member.

The spacer may be in the form of a second rigid plate also having a plurality of openings therethrough which communicate with the plurality of openings in the first plate. The openings in both the first and second plates may be in the form of elongated slots which, on each plate, extend in a parallel direction. In order to form the pores, the parallel slots on each plate are angularly offset from one another with the amount of angular deviation determining the pore size with the largest pore size occurring when the parallel slots on each plate are oriented at an acute angle to one another.

The spacer may also be in the form of discreet protrusions or posts formed in the outer surface of the base member or may be in the form of parallel ribs extending across the outer surface of the base member. The outer rigid plate would then be affixed by an convenient manner to these protrusions. For example, if the base member and plates are made of metal, resistance welding or diffusion bonding may be utilized to form an integral structure. If the base member is a fiber-reinforced thermosetting resin structure then the plate may be attached as part of the thermosetting process or may be affixed to the surface by suitable bonding agents.

The spacers and the outer rigid plate may be placed in a recessed area of the outer surface of the base member. This recessed area has a predetermined shape and depth which cooperates with the spacer and plate thickness to place the outer surface of the rigid plate continuous with the nonrecessed area of the outer surface.

It should be noted that the fixation surface of the present invention can be utilized in both cementless and cemented applications. In a cementless application, the pore size is controlled to induce tissue ingrowth into the porous structure and the orientation is designed to resist stresses transferred directly from the bone. In a cemented application the pore size and orientation is designed to produce better adhesion between the cement and the prosthesis and better resistance to anticipated loading.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

In the drawings, wherein similar reference characters denote similar elements throughout the several views:

FIG. 4 is a side view of the rigid tissue ingrowth plates of the present invention;

FIG. 5 is an exploded isometric view showing the orientation of the rigid plates of FIG. 4 prior to insertion into a recess in the prosthesis of FIG. 1;

FIG. 6 is a cross-sectional view of a prosthesis having the tissue ingrowth surface of the present invention bonded thereto adjacent a bony surface after implantation;

FIG. 7 is an exploded plan view of a tibial prosthesis having the rigid plates of the present invention as fixation surfaces prior to assembly;

FIG. 8 is the prosthesis shown in FIG. 7 after assembly of the rigid plates to the tibial base member;

FIG. 9 is a side view partially in cross-section along lines 9—9 of FIG. 8;

FIG. lo is an exploded plan view of an alternate embodiment for the fixation surface of the present invention utilized as a tibial implant:

FIG. 11 is a cross-sectional view through the alternate embodiment of FIG. 10 after assembly;

FIG. 12 is yet an additional embodiment of the fixation surface of the present invention as a tibial implant in an exploded plan view; and FIG. 13 is a cross-sectional view of the embodiment shown in FIG. 12 after assembly.

DESCRIPTION OF THE PREFERRED EMBODIMENTS

Figure 1:
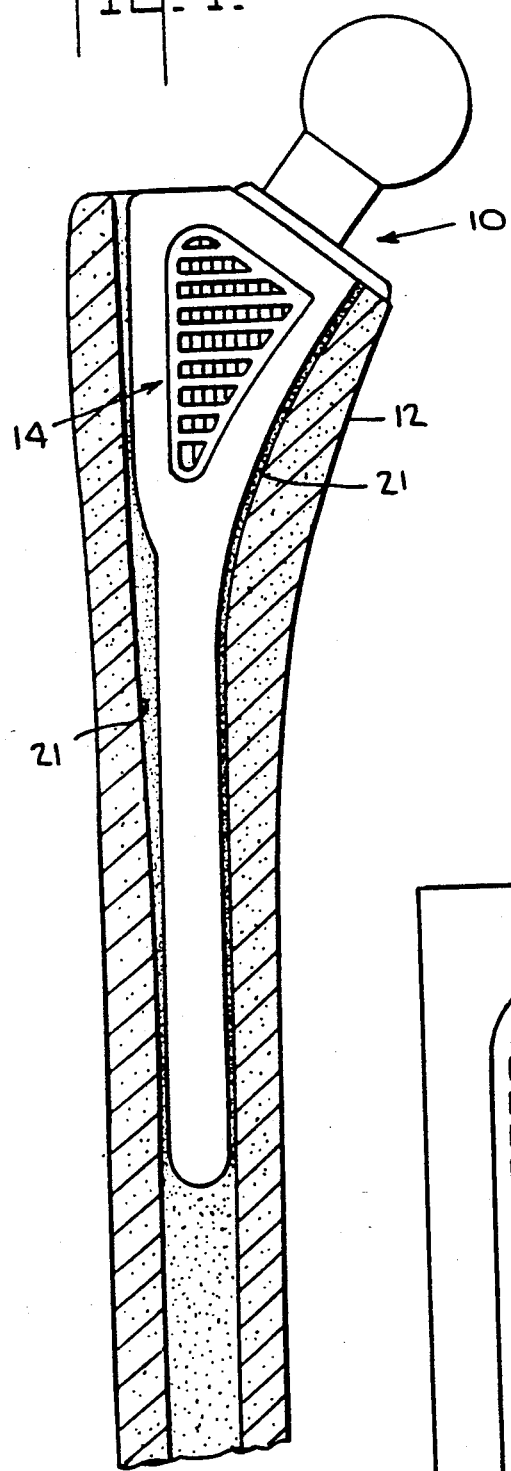
FIG. 1 is a view in the medial-lateral plane of an implanted hip prosthesis having the fixation surface of the present invention with the bone cut away.
Figure 3:
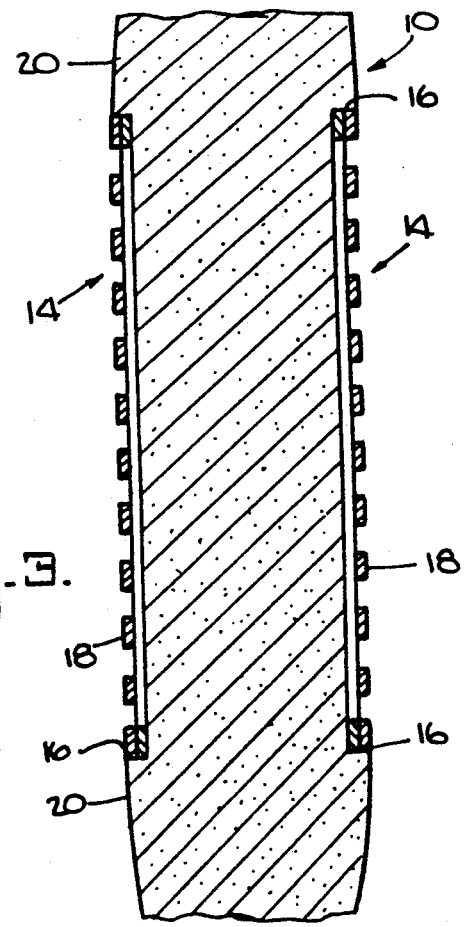
FIG. 3 is a cross-sectional view of the prosthesis along lines 3—3 of FIG. 2.
Figure 2:
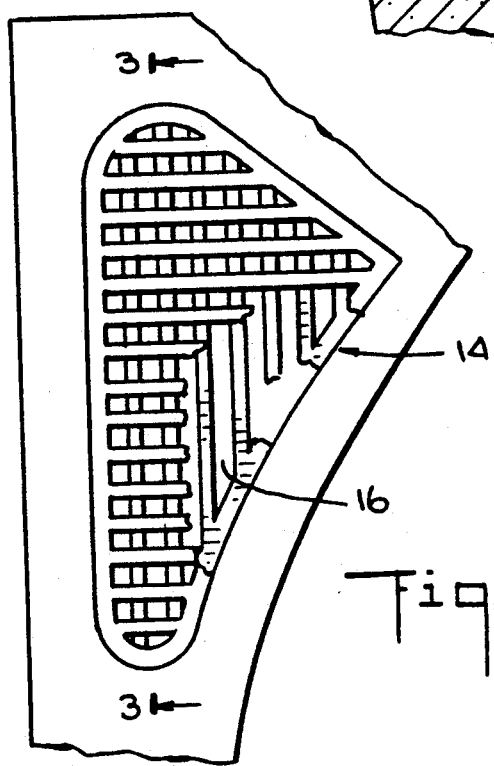
FIG. 2 is an enlarged view of the fixation surface shown in FIG. 1.

Referring to FIGS. 1-6 there is shown a hip prosthesis generally denoted as 10 incorporating the fixation surface of the present invention implanted in a femur 12. The femur 12 of FIG. 1 is cut away in the medial-lateral plane to expose the fixation surface generally denoted as 14. Fixation surface 14 is preferably located in a recess 16 formed on both the anterior and posterior sides of femoral implant 10.

In the preferred embodiment, the fixation surface has the same shape as recess 16 and has a thickness equal to the depth of recess 16 so that an outer surface 18 thereof is continuous with the outer surface 20 of femoral component 10. Both outer surfaces 18 and 20 are adjacent inner surface 21 of femur 12. While fixation surfaces 14 are shown located in the medial-lateral plane of the proximal end of the femoral component 10, it is contemplated that fixation surface 14 may be placed at any desired location about the prosthesis and may be curved if necessary to conform to rounded parts of prosthesis 10.

Referring to FIGS. 4 and 5, it can be seen that fixation surface 14 includes a spacer plate 22 and an outer plate 24. The preferred plates 22 and 24 have elongated slots 26 and 28 respectively, formed therein. In the preferred embodiments, slots 26 of plate 22 are oriented parallel to one another and slots 28 of plate 24 are oriented parallel to one another. Plates 22 and 24 have a shape conforming to the shape of recess 16 formed in the anterior and posterior sides of prosthesis 10. Inner plate 22 is designed to conform to and lay flat against the bottom surface 25 of recess 16.

As can be best seen in FIG. 5, plates 22 and 24 are placed on top of one another and then placed into recess 16 during fabrication of prosthesis 10. If prosthesis 10 and plates 22 and 24 are made of titanium, then the plates are fixedly attached to prosthesis 10 by either electron beam welding, resistance welding, laser welding or diffusion bonding so that they form an integral part of the prosthesis prior to implanatation outer surface 18 of plate 24 is adjacent an exposed surface 21 of, in the case of femur 12, the medullary canal. While in the preferred embodiment surface 18 is continuous with the surface 20 of the prosthesis adjacent the recessed area, it may be positioned slightly above surface 20 to insure contact between surface 21 and surface 18.

Referring again to FIG. 4, it can be seen that parallel slots 26 of plate 22 are oriented perpendicularly with respect to parallel slots 28 in plate 24. It can be seen that by varying the angular orientation of slots 26 and 28 with respect to one another between 0° and 90°, openings or pores of various sizes and shapes are produced. The pores can be made very small or relatively large depending on the angular orientation. All that is required is that there is some communication between openings 26 and 28 to allow tissue to grow into the structure and around cross-members 27 and 29 to thereby lock the prosthesis to the bone structure. It can be seen that while in the preferred embodiment, two plates are utilized to form the porous ingrowth structure, three or even more plates could be utilized to form even more intricate variations in pore size and orientation. Furthermore, other opening patterns such as holes, zig-zag slots or polygonal openings can be used on each plate instead of parallel slots.

The porosity of the structure can also be varied by varying the width of elongated slots 26, 28 and therefore the width of cross-members 27, 29. In the preferred embodiment, the slot width is approximately 1 mm with the cross-members separating the elongated slots having a width of about 1.3 mm. Preferably, plates 22 and 24 have a thickness of at least 0.7 mm and the flexibility of the plates can be varied by varying the material thickness. Utilizing two plates with the dimensions described above, and with the elongated slots and cross-members oriented at 45° results in pore openings of approximately 1 mm×1 mm, with 0.7 mm×1.0 mm, interconnecting passages. This structure is about 55% porous by volume.

Referring now to FIGS. 7 to 9, there is shown a tibial implant generally denoted as 40 in which plates 42 and 44 are designed to fit in a recessed area 46 formed in the tibial tray 48. Again, each plate 42, 44 includes elongated slots 50 and 52 respectively, which in turn define cross-members 54 and 56. Again, slots 50 and cross-members 54 of plate 42 are oriented parallel thereon and slots 52 and cross-members 56 of plate 44 are likewise oriented parallel on that plate. As described herein above, the plates are affixed to a metallic tibial tray 48 by electron beam welding, laser welding or resistance welding or via thermal diffusion bonding. The pore size may be varied as described above and the orientation of the pore structure will be that best suited to resist transverse forces applied to the tibial prosthesis after implantation.

Referring to FIGS. 10 and 11, there is shown an alternate embodiment of the porous fixation surface of the present invention. While the embodiments shown in FIGS. 10 and 11 refer to a tibial implant, the invention disclosed could be utilized equally well on a hip implant or any other suitable prosthetic device. In this embodiment, a plate 60, identical in form to plate 42 previously described, is placed in a recess 61 formed in a tibial tray 62 which recess includes a plurality of integrally formed parallel ribs 64 extending outwardly of the surface thereof.

Ribs 64 are preferably cast or forged onto surface 66 of recess 61. Ribs 64 serve to space plate 60 from surface 66 of recess 61 of tibial tray 62. In the preferred embodiment, ribs 64 are again oriented parallel to one another and, after bonding, a structure exhibits the same porosity as the fixation surface previously described.

Referring to FIGS. 12 and 13, there is shown yet another alternate embodiment in which a plate 70 is spaced above a surface 72 of a recess 71 in a tibial tray 74 by a plurality of posts 76. After bonding plate 70 to tibial tray 74, a much more open structure is formed in this embodiment and, if necessary, a second plate (not shown) exhibiting the same structure of parallel slots and cross-members may be bonded to post 76 and, in turn, plate 70 to form the necessary pore structure.

The method of fabricating the structure set forth above will now be described. The plates may be produced from thin sheet material, such as titanium sheet, with the slots therein cut by programmable laser cutting, photo chemical etching, water jet cutting, wire electrode discharge machining (EDM) or die stamping and conventional machining. The preferred method for attaching the plates to the metal base structure is the use of thermal diffusion bonding. For this process, the plates are thoroughly cleaned and etched in a 9.1% HNO$_3$—HF solution. The plates are then temporarily bonded into the cavity formed in the base member in a few drops of cyanoacrylate adhesive. The plates are then metallurgically bonded in place by diffusion bonding in a fixture designed to take advantage of differential thermal expansion to generate the pressure required to accelerate this bonding. Diffusion bonding does not produce any melting but produces complete bonding across the interface of the parts to be joined. Diffusion bonding is preferred because the plates of the present invention have planar contact surfaces and form an incompressible porous structure. This allows for full transmission of pressure during the diffusion bonding operation.

Metallurgical bonding is achieved in a 1 hour thermal cycle at approximately 1650° F. in a vacuum furnace in an atmosphere of $10^-$ torr. Full interfacial bonds are achieved in this manner both as to the base member and the spacing plate and the spacing plate to the outer plate. In the case of titanium, the implant assembly is chemically milled to remove all traces of an oxygen enriched alpha case which would impair the peak performance of the titanium implant. The prosthesis is then finished via abrasive belting, grinding and machining as is normal in completing the manufacturing cycle.

In order to better resist forces applied to the prosthesis after implantation, the plates are placed in the recesses such that the cross-members of the outermost plate are oriented perpendicular to the anticipated loading. In a hip prosthesis this would mean the cross-members would be oriented perpendicular to the long axis of the prosthesis stem. When the fixation structure of the present invention is utilized in a knee prosthesis tibial tray, the outer cross-members should be oriented at approximately 45° to the long axis of the tray to achieve a biased pore and rib alignment suitable for resisting transverse shifting loads experienced in the knee.

While several examples of the present invention have been described, it is obvious that many changes and modifications may be made thereunto without departing from the spirit and scope of the invention.

I claim:

1. A prosthetic orthopaedic implant comprising:
   a base member defining an outer surface for implantation adjacent a prepared bone surface;
   spacer means fixed to at least a portion of said outer surface of said base member; and
   at least one plate having a plurality of cross-members, each cross-member extending a predetermined length across a substantial portion of said plate wherein adjacent cross-members are separated continuously along the length thereof by an elongated opening therethrough, said plate fixed to said spacer means and spaced a predetermined distance from said outer surface of said base member by said spacer means.

2. The prosthetic implant as set forth in claim 1 wherein said spacer means is a second plate having a plurality of cross-members separated by a plurality of openings therethrough, said plurality of openings in said second plate communicating with said plurality of openings in said at least one plate.

3. The prosthetic implant as set forth in claim 2 wherein said cross-members of said second plate extend across a substantial portion of said plate and said openings in said second plate are elongated slots.

4. The prosthetic implant as set forth in claim 2 wherein said second plate has a thickness of greater than 0.7 millimeters.

5. The prosthetic implant as set forth in claim 2 wherein said cross-members and said openings in each of said at least one plate and said second plate are parallel cross-members separated by parallel elongated slots therebetween, said parallel cross-members on said first plate being angularly offset from said parallel cross-members on said second plate.

6. The prosthetic implant as set forth in claim 5 wherein said parallel cross-members on said second plate extend in a direction perpendicular to the direction of forces generated on the prosthetic implant along said prepared bone surface after implantation.

7. The prosthetic implant as set forth in claim 1 wherein said plate has a thickness of greater than 0.7 millimeters.

8. The prosthetic implant as set forth in claim 1 wherein said openings are elongated slots extending across said at least one plate.

9. The prosthetic implant as set forth in claim 8 wherein said cross-members said elongated slots are disposed in parallel relationship.

10. The prosthetic implant as set forth in claim 1 wherein said spacer means consists of a plurality of protrusions integrally formed on said outer surface of said base member.

11. The prosthetic implant as set forth in claim 10 wherein said plurality of protrusions are in the form of parallel ribs extending across said outer surface of said base member.

12. The prosthetic implant as set forth in claim 1 wherein said outer surface of said base member includes a recessed area of predetermined shape and depth and wherein said spacer means spaces an outer side of said at least one plate so as to form a continuous surface with a non-recessed area of said outer surface.

13. The prosthetic implant as set forth in claim 1 wherein said base member, said spacer means and said plate are made of metal.

14. A prosthetic orthopaedic implant comprising:
a metal base member defining an outer surface for implantation adjacent a prepared bone surface, said outer surface including a recessed area of predetermined shape and depth;
a first metal plate having said predetermined shape and having a plurality of cross-members having a predetermined length separated continuously along the length thereof by elongated slots, said plate fixedly attached to said recessed area of said base member; and
a second metal plate having said predetermined shape and having a plurality of cross-members separated by elongated slots fixedly coupled to said first metal plate, said cross-members of said second plate angularly offset with respect to said cross-members in said first plate.

15. The prosthetic implant as set forth in claim 14 wherein said cross-members on said second plate extend across said second plate in parallel relationship.

16. The prosthetic implant as set forth in claim 15 wherein said cross-members on said second plate extend in a direction perpendicular to the direction of forces generated on the prosthetic implant along said prepared bone surface after implantation.

17. The prosthetic implant as set forth in claim 15 wherein said first and second metal plates each have a thickness of greater than 0.7 millimeters.

18. The prosthetic implant as set forth in claim 17 wherein the width of said elongated slots and said cross-members therebetween in both of said first and second metal plates is at least 1 millimeter.

19. The prosthetic implant as set forth in claim 17 wherein said elongated slots on said first metal plate are oriented at 45° with respect to the elongated slots on said second plate.

20. The prosthetic implant as set forth in claim 14 wherein said outer surface of said base member includes a recessed area of predetermined shape and depth and wherein said spacer means spacers an outer side of said second plate so as to form a continuous surface with a non-recessed area of said outer surface.

* * * * *